Figure 1:
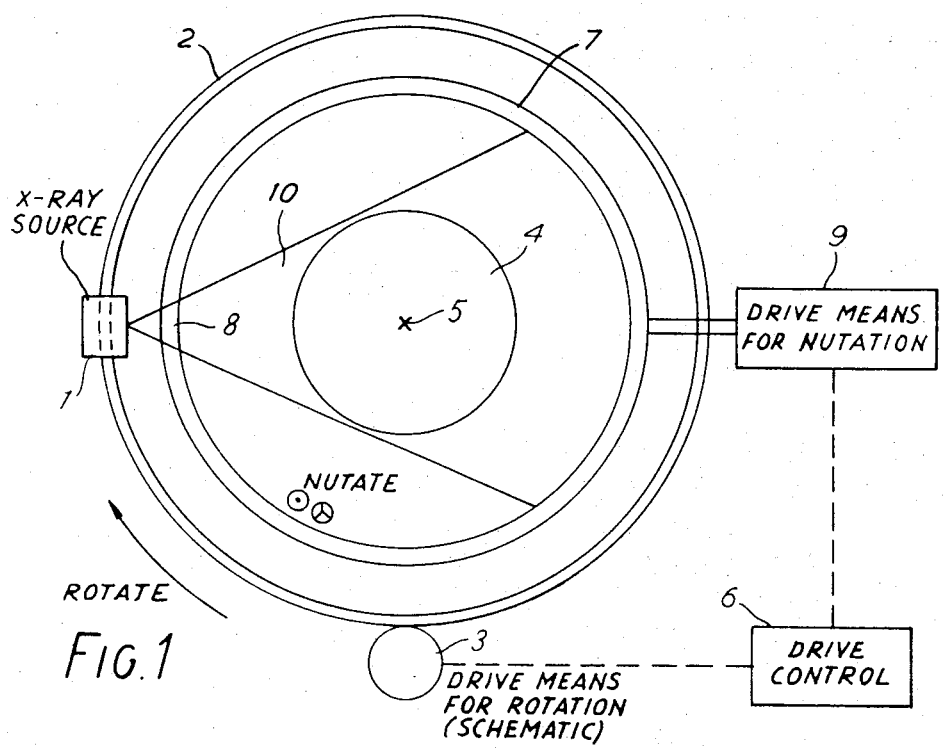

United States Patent [19]

Moore

[11] Patent Number: 4,504,962

[45] Date of Patent: Mar. 12, 1985

[54] COMPUTERIZED TOMOGRAPHY

[75] Inventor: John F. Moore, Lake Bluff, Ill.

[73] Assignee: EMI Limited, Hayes, England

[21] Appl. No.: 972,391

[22] Filed: Dec. 22, 1978

[51] Int. Cl.³ .............................................. G03B 41/16
[52] U.S. Cl. ........................................ 378/19; 378/10
[58] Field of Search .................... 250/445 T, 366, 367, 250/385; 378/19

[56] References Cited

U.S. PATENT DOCUMENTS 3,973,128  8/1976  Le May ........................... 250/445 T

Primary Examiner—Craig E. Church

[57] ABSTRACT

A computerized tomographic scanner which includes detectors that do not rotate around the patient's body includes means for combining the outputs of adjacent detectors in groups of different sizes (e.g. groups of 2, 4 or 8), or for utilizing the outputs individually, in dependence upon the resolution and speed requirements of the scan.

10 Claims, 4 Drawing Figures

COMPUTERIZED TOMOGRAPHY

The present invention relates to computerized tomography, a radiographic technique for examining cross-sectional slices of patients by means of X-radiation.

Computerized Tomography was invented by Godfrey N. Hounsfield of the English firm EMI Limited, and the technique is described, inter alia, in his U.S. Pat. No. 3,778,614. Inspection of that patent will readily reveal that the technique involves the acquisition of data from which can be ascertained the attenuation, suffered by X-radiation, on traversing each of many substantially linear paths across one of the aforementioned slices and the processing, by compensated layergramming, of the data so acquired to produce a representation which shown accurately the variation of opacity to the exploring radiation from point to point over the slice.

One technique for acquiring the necessary data that has recently become widely accepted involves the rotation of a source fan of X-radiation around the patient about an axis which intersects the slice substantially normally; the patient being surrounded by a ring of detectors, centered on the said axis, which do not take part in the rotational movement and the present invention has particular relevance to computerized tomographic scanners utilizing this technique.

The source may, in rotating, follow a locus of smaller diameter than the detector ring, as described in Christopher A. G. Lemay's U.S. Pat. No. 4,031,395 (this configuration referred to hereinafter as "rotate-fixed") or it may follow a locus of larger diameter than the detector ring as described in Richard W. Fetter's U.S. patent application Ser. No. 811,279 filed june 29, 1977 (now U.S. Pat. No. 4,137,455). In this latter case (which is referred to hereinafter as "rotate-nutate"), the detector ring has to nutate in a direction perpendicular to the slice under examination to prevent detectors disposed between the source and the body interrupting the radiation. Such nutation, and means for causing it, is fully described in the aforementioned patent application of Richard W. Fetter, the contents of which application are incorporated herein by reference.

Where a ring of detectors which performs no angular movement around a patient is used, the resolution of the representation of the slices examined thereby tends to be governed by a number of factors which include the speed at which the source moves around the patient, the X-ray power output of the source and the number of detectors included in the ring.

The detector dimensions are usually a compromise between a small size ideally required for high resolution and a larger size ideally required for good X-ray photon collecting efficiency when cooperating with a source of limited power output scanned rapidly around the patient.

One of the objects of this invention is to render computerized tomographic scanners of the rotate-fixed or rotate-nutate kind adaptable in resolution to suit varying operating conditions.

This object is achieved, in accordance with one aspect of the invention, by providing a ring of small detectors and means for selectively combining the outputs of two or more neighbouring detectors to suit the scanning rate imposed on the X-ray source and the power output capability of the source.

It has been disclosed in Christopher A. G. LeMay's U.S. Pat. No. 3,973,128 that, in a computerized tomographic apparatus utilizing a source of a wide fan of radiation which rotates around a patient, the data acquired in relation to radiation in the central part of the fan can be deliberately made to differ in resolution from the data acquired in relation to the radiation in the peripheral parts of the fan.

It is another object of this invention to take advantage of the adaptability in resolution provided by selective combination of detector outputs, as aforementioned, to enable variations in resolution across the fan, as taught by LeMay in his U.S. Pat. No. 3,973,128 patent discussed above, to be implemented in CT scanners of rotate-fixed and rotate-nutate kind.

Figure 2:
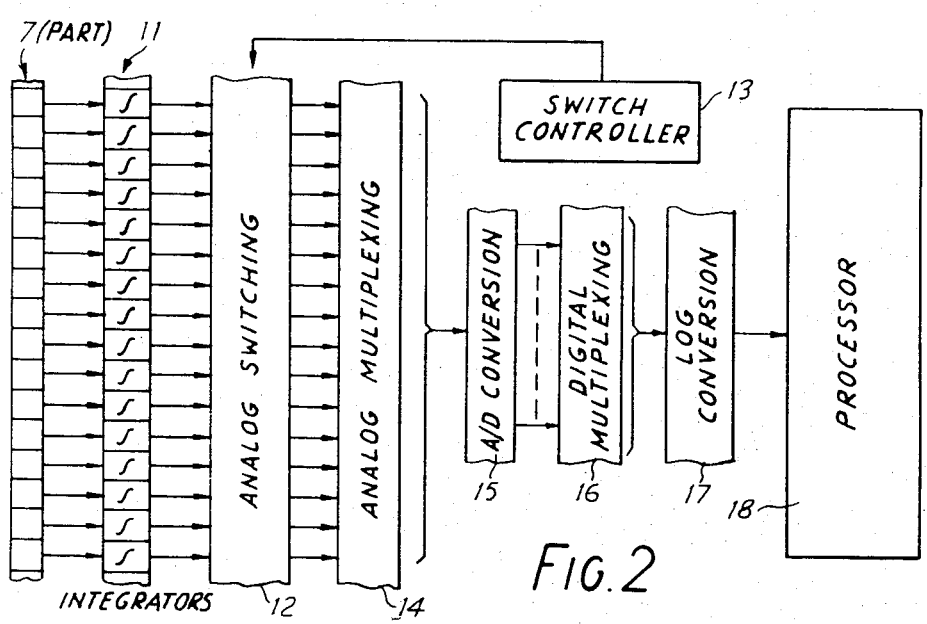
Figure 3:
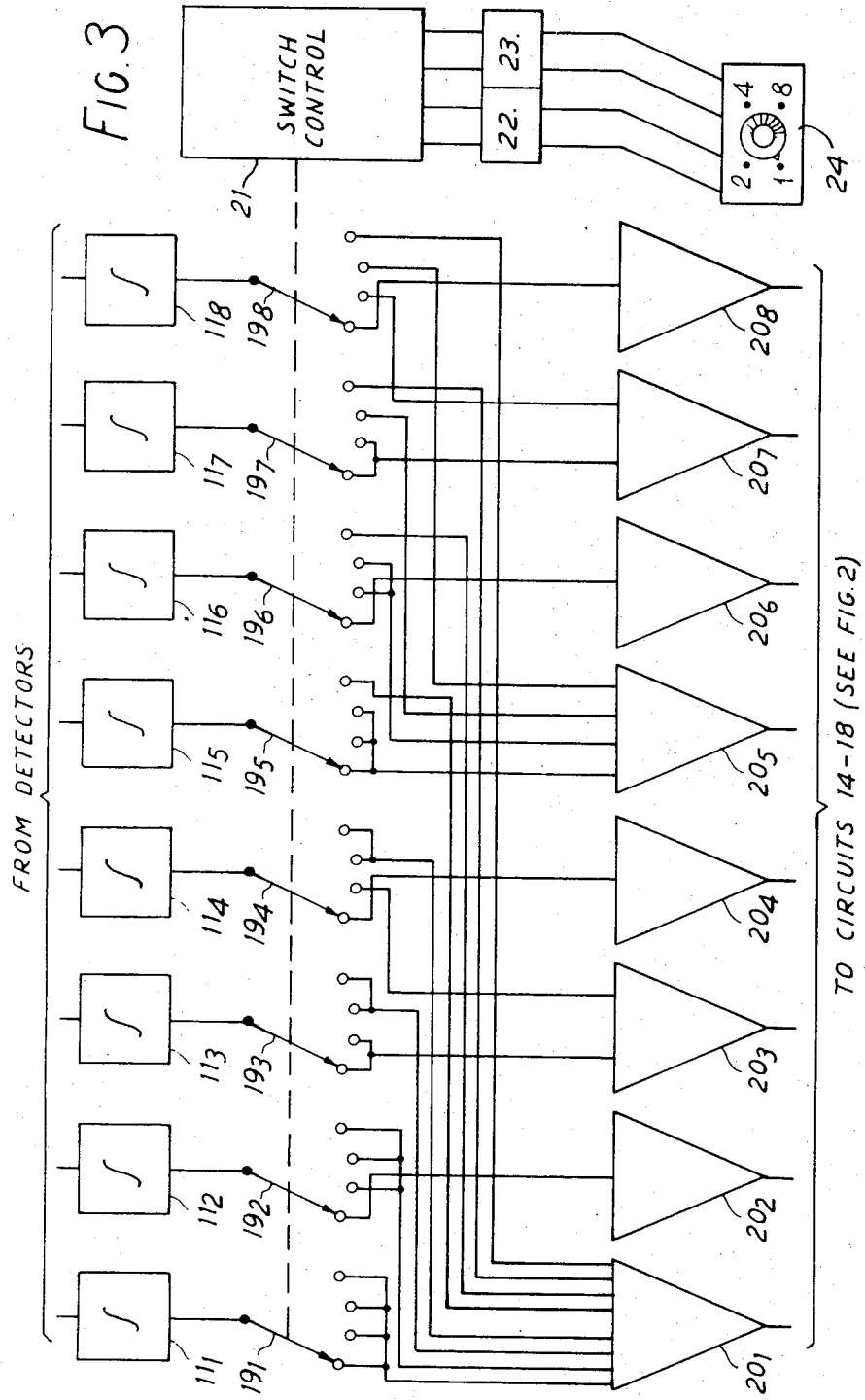
Figure 4:
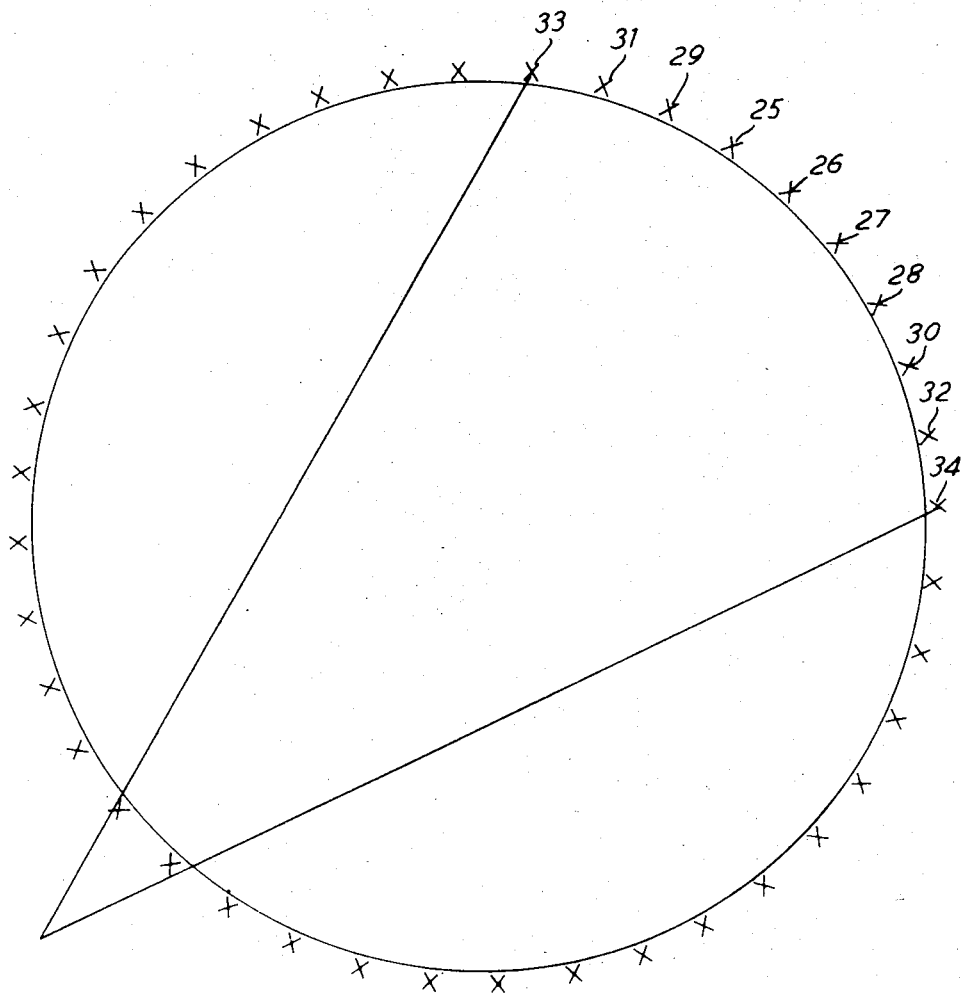

In order that the present invention may be clearly understood and readily carried into effect, one embodiment thereof will now be described, by way of example only, with reference to the accompanying drawings, of which:

FIG. 1 shows, in schematic form, certain elements of a computerized tomographic scanner in accordance with one example of the invention, FIG. 2 shows, on enlarged scale, a section of the detector ring and some associated circuits, FIG. 3 shows, in schematic form, an analog switching arrangement by means of which neighbouring detector outputs can be selectively interconnected, and FIG. 4 is a plan view of detector groups and a radiation spread and is used to explain the apparatus of one aspect of the invention.

FIG. 1 shows, schematically, some elements of a computerized tomographic scanner of rotate-nutate kind, although it is stressed, as previously noted, that the invention is also applicable to computerized tomographic scanners of the rotate-fixed kind. For a full and complete description of a rotate-nutate scanner, the reader's attention is respectfully directed to the aforementioned patent application in the name of Richard W. Fetter. It is deemed sufficient for the purposes of this application, however, to refer to FIG. 1 of the accompanying drawings, wherein an X-ray source 1, for example a rotating anode X-ray tube, is supported on an annular frame 2 which is rotatable by drive means 3 around a body 4. The rotation of the source is executed about an axis 5 extending longitudinally of the body; the axis 5 being disposed, in operation, horizontally since the patient lies prone or supine for the examination. The drive means 3 is controlled by control means 6 to rotate the source 1 around the body 4 at a constant rate.

A ring 7 of radiation sensitive detectors surrounds the body 4, the ring being centered on the axis 5 and being of smaller diameter than the locus followed by the source 1 during its rotational movement. In order that parts of the detector ring, such as that shown in 8 in FIG. 1, for the time being disposed at the same side of the body as the source do not interrupt the X-radiation, the ring is caused to nutate in a direction perpendicular to the plane of the paper so that parts such as 8 of the detector ring 7 are moved out of the way of the radiation. The nutating movement is effected by means schematically shown as a block 9 and an interconnection is shown between block 9 and the control means 6 to indicate that the rotational movement of the source 1 and the nutating movements of the ring 7 are synchronized. In practice, the synchronization may be effected mechanically.

The source 1 produces a planar, fan-shaped spread 10 of radiation of sufficient breadth to accommodate the body 4 with some surplus so that radiation which has not suffered attenuation by traversing any part of the body is admitted to the detector ring at least on one side of the spread 10. Such unattenuated radiation can be used for calibration purposes, and it will readily be observed that as the source 1 rotates around the body 4 the unattenuated radiation will sweep around the detector ring, thus affording sequentially calibration data for all of the detectors in the ring.

Detectors which fall within the spread of radiation at any time (other than those receiving unattenuated radiation) provide (if suitably collimated by means which are not shown but are well known to those skilled in the art) output signals indicative of the amounts of radiation emergent from the body along substantially straight paths from the source. From these output signals, and a knowledge of the amount of radiation transmitted into the body at the relevant time, the attenuation suffered by the radiation on traversing each path can be ascertained. The attenuation values so ascertained, after calibration in the light of the receipt, as aforementioned, of unattenuated radiation, are processed, for example as described in the Hounsfield patent referred to above or as described in Christopher A. G. LeMay's U.S. Pat. No. 3,924,129, or in any other suitable way, to produce a representation of the cross-sectional slice of body 4 irradiated by the source 1.

Utilization of this example of the invention permits the individual detectors included in the ring 7 to be made substantially smaller than has hitherto been the case. For example, a single silicon chip, similar in size to that currently used for about eight detectors may now be constructed to include 16, 32, or 64 detectors. The various circuits shown in FIG. 2, i.e. integrators 11, analog switching circuits 12—used to implement the adaptive nature of the invention and described in more detail hereinafter—analog multiplexing circuits 14, analog-to-digital conversion circuits 15, digital multiplexing circuits 16 and optionally/logarithmic conversion circuits 17 can also be formed on the same chip. The control circuit for the analog switching circuits is shown at 13 and the processing circuits for processing the detector data to produce the desired representation are shown at 18.

It will be appreciated that each detector comprises a scintillator material and an associated photosensitive area which responds to light output from its respective piece of scintillator material to provide an electrical output signal. Typically the photosensitive area is constituted by a photovoltaically operated semiconductor diode.

In utilizing the invention, the electrical output signals derived from a variable number of adjacent detectors can be combined to suit the operating capabilities of the scanner. For example, the number of detector channels combined may be made proportional to scan speed and inversely proportional to the available X-ray power.

Thus a high power, low speed scan could be used to give high resolution; the detector channels being processed individually. If the available power were restricted and/or the scan speed increased, then adjacent detector channels could be combined in groups of (for example) two, four or eight. Thus scan speed can be directly traded off with resolution.

The adaptability provided by the invention can also be used to enable scanners of different performances, designed to fulfill different market requirements, to share common detector/electronics constructions, which is economically desirable. For example, a relatively low cost scanner may have its detectors permanently tied together in eights whereas another kind of scanner may have its detectors permanently tied together in pairs or in fours or may be adaptable in situ, as described hereinafter, by means of analog switching. The adaptability also enables a low cost scanner to be up-graded in performance without changing the detector assembly. The only addition called for would be the multiplexing electronics.

In situ adaptive switching can be used to implement variable resolution across the distribution 10 of radiation in that directors for the time being irradiated by radiation in the central part of the fan may be treated individually or tied in pairs and the detectors for the time being irradiated by the peripheral parts of the spread may be tied together in, for example, fours or eights. This reduces the amount of data to be handled without seriously degrading the representation of the body slice. The groupings of detectors may, if desired, be caused to vary progressively across the fan. Since the group of detectors irradiated by the spread 10 is constantly changing, it will be appreciated that the necessary switching of detector outputs must correspondingly change during the rotation of the source 1 around the body 4. In one particularly advantageous arrangement of this kind (i.e. with variable resolution) high resolution data may be obtained in relation to a relatively small region of interest within the body. Radiation traversing the body outside that region can be attenuated by a suitably shaped wedge, by a factor of (say) ten and the detectors receiving this attenuated radiation can be grouped together to provide output signals of convenient magnitude and resolution in respect of body material other than that disposed in the region of interest.

FIG. 3 shows schematically the analog switching 12 and control 13 thereof associated with one group of eight adjacent detectors. The integrators $11_1$–$11_8$ for those eight detectors are shown, and they feed respective switchable means $19_1$–$19_8$; each switchable means having four set positions, one for each desired combination of detectors (singly, in pairs, in fours or in eights). The switchable means $19_1$–$19_8$ are shown for simplicity as ganged mechanical switches but it will be appreciated that, in practice, they will be constituted by suitable electronic analog switch devices.

The switch devices $19_1$–$19_8$ feed respective summing amplifiers $20_1$–$20_8$, which feed the further circuits shown at 14–18 in FIG. 2. The control for the devices $19_1$–$19_8$ is shown at 21 and it is effective to set all of the devices $19_1$–$19_8$ in the same one of the four positions in dependence upon a two bit digital code applied thereto from a pair of bistable circuits 22, 23 which are respectively set to their 0 or 1 conditions in dependence upon the setting of a four position manual controller 24. The manual controller 24 causes the two bistable circuits to assume a selected one of the four possible settings 00, 01, 10 and 11, and each setting covers the control circuit 21 to set all of the switch devices $19_1$–$19_8$ to the same one of the four positions shown in the drawings in dependence upon the circumstances of the scanning as described previously.

In one example, the circuit responds to the setting 00 to cause the switch devices $19_1$–$19_8$ to assume the positions shown in the drawing, thus treating the detector outputs singly. The setting 01 causes the switch devices to move to their second positions in which the detector outputs are grouped in pairs. Settings 10 and 11 cause the detector outputs to be grouped in fours and eights respectively.

In the foregoing circumstances, all groups of eight adjacent detectors (typically there are 1000 such groups) are similarly controlled by identical signals from the control circuit 21.

If it is desired to enable the scanner to operate with variable resolution across the spread of 10 of radiation, then the different groups of detectors need to be controlled differently in accordance with the progress of the source of radiation around the patient's body. In the example shown in FIG. 4, it is assumed that only 40 groups of eight detectors are used, for ease of illustration, but the principle of operation remains the same however many detectors are actually used.

As shown, each detector group is indicated by a cross and it can be seen that, in any one position of the spread of radiation, ten of the 40 detector groups are irradiated. In this example, the analog switching of detector outputs is so controlled that the outputs from the four detector groups 25-28 disposed centrally of the radiation spread are used singly; the outputs from the two detector groups 29 and 30 adjacent the four central ones are grouped in pairs; the outputs from the two detector groups 31 and 32 adjacent the groups 29 and 30 but nearer the edges of the spread of radiation are grouped in fours and finally the outputs from detector groups 33 and 34, disposed at the edges of the spread of radiation, are grouped in eights. It is stressed that the grouping arrangement described above is only exemplary and that many other arrangements can be used. In particular, it may be preferable to arrange that outputs derived from detector groups at the very edges of the fan, where the radiation is unattenuated and can be used for calibration purposes as aforementioned, are used singly.

It will be appreciated that, if the detector outputs are grouped as described above, the control for the analog switching has to vary for different groups and that such switching is preferably performed automatically and controlled by the current position of the X-ray source. This control can be derived by means of a graticule provided in known manner on the scanning frame of the machine and arranged, in known manner, to co-operate with a photocell device to produce electrical timing signals indicative of the progress of the scan. These timing signals can then be used to cause the control circuit 24 to change the grouping of detector outputs appropriately. The control circuit 24 requires, of course, an individual output connection to each group of eight detectors.

Assuming that it is desired to selectively combine the output signals from adjacent detectors in twos, fours or eights or to be able to use them individually, a coded control scheme which is economic in the number of bits required is described below.

It would, on the face of it, appear that if sixteen detectors were to be grouped in any of four ways, then 6 bits (two bits for the scheme selection and four bits to identify the detectors concerned) would be required. Unique selection and control can however, be achieved using only five bits as follows:

| Detector No. | Scheme | Identity |
| --- | --- | --- |
| 0 | 0 | 0000 |
| 1 | 0 | 0001 |
| 2 | 0 | 0010 |
| . | . | . |
| 15 | 0 | 1111 |

| Detector Nos. | Scheme | Free | Identity |
| --- | --- | --- | --- |
| For individual operation. | | | |
| 0,1 | 1 | 0 | 000 |
| 2,3 | 1 | 0 | 001 |
| 4,5 | 1 | 0 | 010 |
| . | . | . | . |
| 14,15 | 1 | 0 | 111 |
| For Grouping in pairs. | | | |
| 0,1,2,3 | 11 | 0 | 00 |
| 4,5,6,7 | 11 | 0 | 01 |
| 8,9,10,11 | 11 | 0 | 10 |
| 12,13,14,15 | 11 | 0 | 11 |
| For grouping in fours. | | | |
| 0-7 | 111 | 0 | 0 |
| 8-15 | 111 | 0 | 1 |
| For grouping in eights. | | | |

Thus the grouping of any batch of 16 adjacent detectors can be controlled under the influence of a 5-bit scheme.

It is to be noted that the invention is not restricted to its application to the practical embodiments described hereinbefore. In particular, the integrators 11 shown in FIGS. 2 and 3 may be dispensed with and the data, summed as appropriate, can be sampled in known manner to produce signals relating to substantially linear beam paths across the body slice under examination. In such a case, preamplifying circuits can be connected in place of the integrators 11.

What I claim is:

1. A computerized tomography method comprising the steps of providing a plurality of detector devices distributed around a patient position, projecting a substantially planar, fan-shaped distribution of X-radiation through a sectional slice of the body of a patient, disposed at said patient position, from many different positions distributed angularly around said patient position, causing said detector devices to provide electrical output signals indicative of the radiation emerging from said slice of the body of a patient along a plurality of mutually divergent directions from each of said positions, providing a processor, and selectively passing, to said processor, individual electrical output signals provided by individual detector devices or combination electrical signals generated by combining the electrical output signals provided by respective groups of neighboring detector devices, the numbers of devices in such groups being selectable, and causing said processor to process the signals selectively passed to the processor to generate, in part from said electrical output signals or combination electrical signals selectively passed thereto, electrical data signals indicative of the attenuation suffered by the X-radiation passing through the slice along various directions and to generate, in part from said electrical data signals, a representation of the variation of an X-ray response characteristic over said slice.

2. A computerized tomography method comprising the steps of providing a plurality of detector devices distributed around a patient position and substantially incapable of angular movement around said position, projecting a substantially planar, fan-shaped distribution of X-radiation through a sectional slice of the body of a patient, disposed at said patient position, from many different positions distributed angularly at least halfway around said patient position, causing said detector devices to provide electrical output signals indicative of the radiation emergent from said slice of the body of a patient along a plurality of mutually divergent directions from each of said positions, providing a processor and selectively passing, to said processor, individual electrical output signals provided by individual detector devices or combination electrical signals generated by combining the electrical output signals provided by respective groups of neighboring detector devices, the numbers of devices in such groups being selectable, and causing said processor to process the signals selectively passed to the processor to generate, in part from said electrical output signals or combination electrical signals selectively passed thereto, electrical data signals indicative of the attenuation suffered by the X-radiation in passing through the slice along various directions and to generate, in part from said electrical data signals, a representation of the variation of an X-ray response characteristic over said slice.

3. A computerized tomographic scanner including detector means, comprising a plurality of detector devices distributed around a patient position and substantially incapable of angular movement around said position, means for projecting a substantially planar, fan-shaped distribution of X-radiation through a sectional slice of the body of a patient, disposed at said patient position, from many different positions distributed angularly at least halfway around said patient position, said detector means providing electrical output signals indicative of the radiation from said slice of the body of a patient along a plurality of mutually divergent directions from each of said positions, a processor, switchable means connected to said detector means and to said processor to selectively pass, to said processor, individual electrical output signals provided by individual detector devices or combination electrical signals generated by combining the electrical output signals provided by respective groups of neighboring detector devices, the numbers of devices in such groups being selectable by means of said switchable means, said processor including means for processing the electrical signals passed to the processor by said switchable means to generate, in part from said electrical output signals or combination electrical output signals, electrical data signals indicative of the attentuation suffered by the X-radiation in passing through the slice along various directions and means for generating, in part from said electrical data signals, a representation of the variation of an X-ray response characteristic over said slice.

4. A computerized tomographic scanner including detector means, comprising a plurality of detector devices distributed around a patient position and substantially incapable of angular movement around said position, a source of a substantially planar, fan-shaped distribution of X-radiation, means for moving said source angularly around said position to project said radiation across a cross-sectional slice of the body of a patient, disposed at said patient position, from many different positions distributed angularly around said patient position, said detector means providing electrical output signals indicative of the amounts of radiation emergent from said slice of the body of a patient along a plurality of mutually divergent beam paths from each of said positions, a processor for processing data indicative of the attenuation suffered by said radiation when traversing the various beam paths to generate a representation of the variation of an X-ray response characteristic over said slice, and switchable means connected to said detector means and adapted to pass, to said processor, data indicative of said amounts of radiation, said switchable means being adapted to selectively pass, to said processor, individual electrical output signals provided by individual detector devices or combination electrical signals generated by combining the electrical output signals provided by respective groups of neighbouring detector devices; the numbers of devices in such groups being selectable by means of said switchable means.

5. A scanner as claimed in claim 2 wherein the electrical output signals remain consistently in the individual or grouped form selected throughout said examination.

6. A scanner according to claim 5 including manually operable means for selecting the number of electrical output signals to be combined.

7. A scanner as claimed in claim 4 wherein said switchable means includes analog switching means for selectively permitting said electrical output signals to be used singly or combined in groups of two, four or eight.

8. A scanner according to claim 7 wherein said switchable means combines electrical output signals in groups which vary in size during said examination.

9. A scanner according to claim 8 wherein said group of variable size vary in dependence upon the position within said distribution at which the detector devices are for the time being disposed.

10. A scanner according to claim 9 wherein electrical output signals for detector devices for the time being disposed centrally of said distribution are combined in smaller groups than electrical output signals from detector devices disposed, for the time being, peripherally of said distribution.

* * * * *